United States Patent
Pascal et al.

(10) Patent No.: US 8,663,092 B2
(45) Date of Patent: Mar. 4, 2014

(54) SYSTEM DEVICE AND METHOD FOR ESTIMATING THE SIZE OF AN OBJECT IN A BODY LUMEN

(75) Inventors: Amit Pascal, Haifa (IL); Eli Horn, Kiryat Motzkin (IL)

(73) Assignee: Given Imaging, Ltd., Yoqneam (IL)

( * ) Notice: Subject to any disclaimer, the term of this patent is extended or adjusted under 35 U.S.C. 154(b) by 1511 days.

(21) Appl. No.: 12/159,303

(22) PCT Filed: Dec. 28, 2006

(86) PCT No.: PCT/IL2006/001504
§ 371 (c)(1),
(2), (4) Date: Nov. 13, 2008

(87) PCT Pub. No.: WO2007/074462
PCT Pub. Date: Jul. 5, 2007

(65) Prior Publication Data
US 2009/0318760 A1    Dec. 24, 2009

Related U.S. Application Data

(60) Provisional application No. 60/754,318, filed on Dec. 29, 2005.

(51) Int. Cl.
*A61B 1/00* (2006.01)
*A61B 1/04* (2006.01)
*A61B 1/06* (2006.01)

(52) U.S. Cl.
USPC ........... 600/117; 600/103; 600/118; 600/160; 600/178

(58) Field of Classification Search
USPC .......................... 600/103, 117, 118, 160, 178
See application file for complete search history.

(56) References Cited

U.S. PATENT DOCUMENTS

| | | | |
|---|---|---|---|
| 3,817,635 A | 6/1974 | Kawahara | |
| 4,986,262 A | 1/1991 | Saito | |
| 5,604,531 A * | 2/1997 | Iddan et al. | 348/76 |
| 5,669,871 A | 9/1997 | Sakiyama | |
| 6,240,312 B1 | 5/2001 | Alfano et al. | |
| 6,682,927 B2 | 1/2004 | Meyer et al. | |
| 7,877,134 B2 * | 1/2011 | Glukhovsky | 600/476 |
| 2001/0035902 A1 | 11/2001 | Iddan et al. | |
| 2002/0107444 A1 * | 8/2002 | Adler | 600/424 |
| 2004/0127785 A1 * | 7/2004 | Davidson et al. | 600/407 |
| 2004/0258328 A1 * | 12/2004 | Adler | 382/286 |

(Continued)

OTHER PUBLICATIONS

International Search Report for International Application No. PCT/IL06/01504, Oct. 9, 2008.

(Continued)

*Primary Examiner* — Philip R Smith
*Assistant Examiner* — Rynae Boler
(74) *Attorney, Agent, or Firm* — Pearl Cohen Zedek Latzer Baratz LLP (57) ABSTRACT

A device, system and method for capturing in-vivo images allows for size or distance estimations for objects within the images. According to one embodiment of the present invention there may be provided, in an in-vivo device at least an imager, an illumination source to provide illumination for the imager, an energy source to emit for example a light beam or a laser beam in a body lumen and a processor to, based on the light beam or laser beam image, estimate, for example the size of objects in a body lumen.

17 Claims, 6 Drawing Sheets

(56) References Cited

U.S. PATENT DOCUMENTS

| | | | |
|---|---|---|---|
| 2005/0043586 A1* | 2/2005 | Suzushima | 600/160 |
| 2005/0096712 A1 | 5/2005 | Abraham-Fuchs et al. | |
| 2005/0240077 A1* | 10/2005 | Rovegno | 600/108 |
| 2005/0281446 A1* | 12/2005 | Glukhovsky et al. | 382/128 |

OTHER PUBLICATIONS

Partial European Search Report for European Application No. 06 83 2272 completed Nov. 10, 2009.

European Search Report for European Patent No. 06832272.6 mailed Feb. 17, 2012.

* cited by examiner

SYSTEM DEVICE AND METHOD FOR ESTIMATING THE SIZE OF AN OBJECT IN A BODY LUMEN

CROSS-REFERENCE TO RELATED APPLICATIONS

This application is a National Phase Application of PCT International Application No. PCT/IL2006/001504, International Filing Date Dec. 28, 2006, which claimed priority from U.S. Patent Application No. Ser. 60/754,318, filed Dec. 29, 2005, which is hereby incorporated by reference.

FIELD OF THE INVENTION

The present invention relates to an in-vivo device, system and method such as for imaging an in-vivo lumen; more specifically, to a method and apparatus in an in-vivo system for estimating the size of an in-vivo object.

BACKGROUND OF THE INVENTION

Known devices may be helpful in providing in-vivo sensing, such as imaging or pH sensing. Autonomous in-vivo sensing devices, such as swallowable or ingestible capsules or other devices may move through a body lumen, sensing as they move along. An autonomous in-vivo sensing device such as an imaging device may include, for example, an imager for obtaining images from inside a body cavity or lumen, such as the gastrointestinal (GI) tract. The imager may, for example, be associated with an optical system, and optionally a transmitter and an antenna. Some of these devices use a wireless connection to transmit image data.

SUMMARY OF THE INVENTION

An embodiment of the device, system and method of the present invention may enable the estimation or determination of the size of objects seen in in-vivo images from within body lumens or cavities, such as the gastrointestinal (GI) tract. According to an embodiment of the invention, calculations according to a certain algorithm(s) are performed on the images in order to present to an observer an estimation of the real size (or distances) of the objects in the image.

According to one embodiment of the invention there may be provided, in an in-vivo imaging device at least an imager, an illumination source to provide illumination for the imager, an energy source to emit for example a light beam or a laser beam in a body lumen and a processor to, based on the laser beam image, determine, for example the size of objects in a body lumen.

According to a further embodiment of the invention there may be provided a method for estimating the size of objects in a body lumen. The method according to one embodiment of the invention may include the steps of emitting light, such as a laser beam optionally from behind an optical dome in an in-vivo imaging device, and estimating the size of objects in a body lumen based the image of the light beam.

BRIEF DESCRIPTION OF THE DRAWINGS

The present invention will be understood and appreciated more fully from the following detailed description taken in conjunction with the drawings in which.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE INVENTION

In the following description, various aspects of the present invention will be described. For purposes of explanation, specific configurations and details are set forth in order to provide a thorough understanding of the present invention. However, it will also be apparent to one skilled in the art that the present invention may be practiced without the specific details presented herein. Furthermore, well known features may be omitted or simplified in order not to obscure the present invention.

Embodiments of the system and method of the present invention may be used in conjunction with an imaging system or device such as embodiments described in U.S. Pat. No. 5,604,531 to Iddan et al. and/or in US Patent Application, Pub. No. 2001/0035902 entitled A DEVICE AND SYSTEM FOR IN VIVO IMAGING, both of which are hereby incorporated by reference. However, the device, system and method according to the present invention may be used with any suitable device, system and method providing imaging and other data from a body lumen or cavity.

Figure 1:
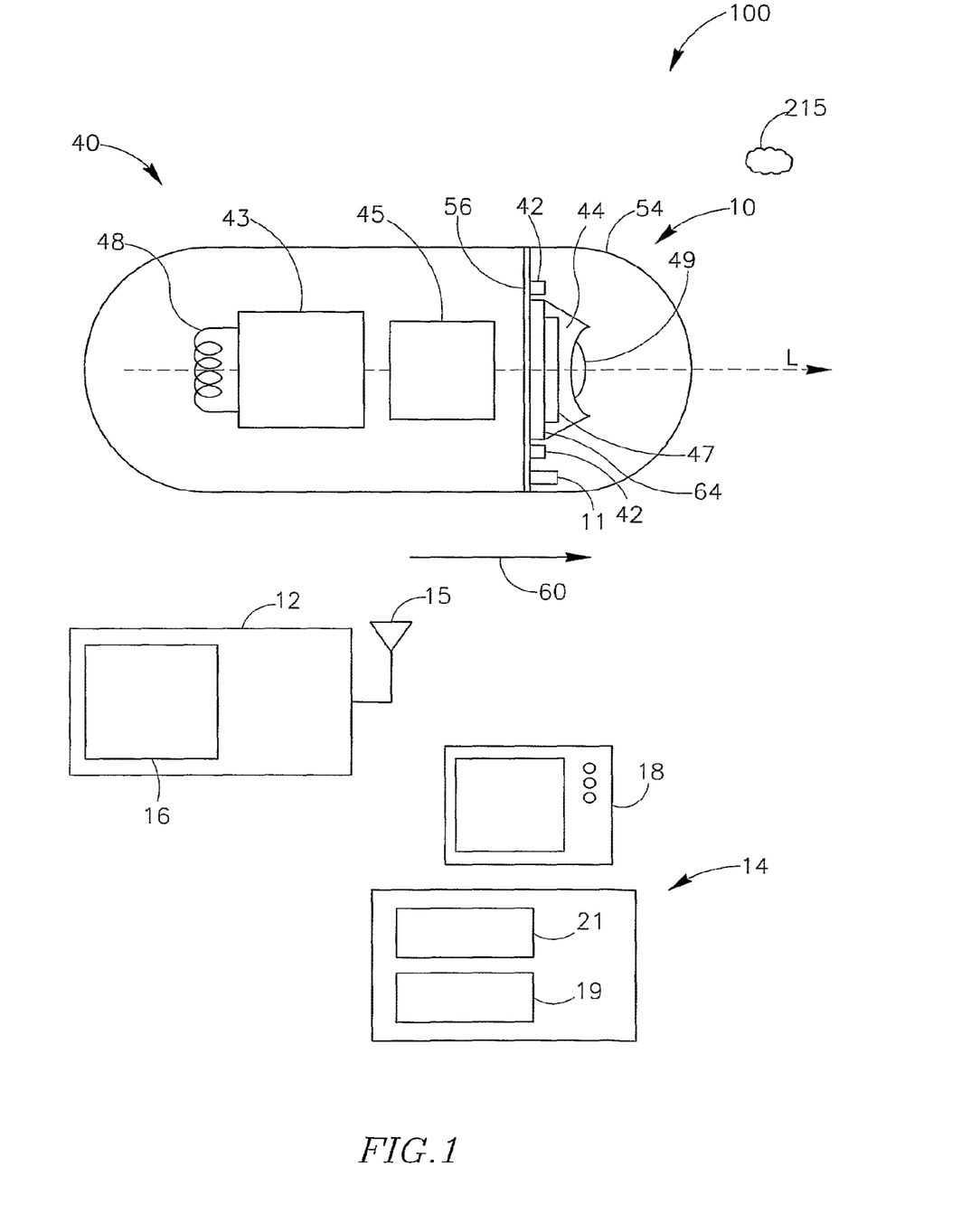
FIG. 1 shows a schematic diagram of an in-vivo imaging system, according to one embodiment of the present invention.

Reference is made to FIG. 1, which shows a schematic diagram of an in-vivo imaging system 100 according to one embodiment of the present invention. The in-vivo imaging system 100 may include, for example an in-vivo imaging device 40. The in-vivo device 40 may be, for example, a swallowable capsule capturing images and possibly other data. The in-vivo device 40 may be in the shape of a capsule, including for example an viewing window or dome 54; other shapes may be used, and the device need not be swallowable or a capsule. Typically, device 40 may include an optical system 10 including, for example, one or more lens(es) 49, lens holder, baffle, or separator 44, a sensor such as an imager 47, for capturing images, and a processing chip or circuit that processes the signals generated by the imager 47. Processing circuit need not be a separate component; for example, processing or a processing chip may be integral to the imager 47. An illumination source(s) 42, such as a set of light emitting diodes (LEDs), organic LEDs (OLEDs), or other suitable light sources, may provide light to illuminate objects.

Embodiments of the device are typically autonomous and are typically self-contained. For example, the device may be a capsule or other unit where all the components are substantially contained within a container or shell, and where the device does not require any wires or cables to, for example, receive power or transmit information. The device may communicate with an external receiving and display system to provide display of data, control, or other functions. For example, power may be provided by an internal battery or a wireless receiving system. Other embodiments may have other configurations and capabilities. For example, components may be distributed over multiple sites or units. Control information may be received from an external source.

According to one embodiment of the present invention, the device 40 typically may include a transmitter/receiver 43, for transmitting and/or receiving image and other (e.g., non-image) information to a receiving device, and may include other components. The transmitter/receiver 43 may be an ultra low power radio frequency (RF) transmitter with high bandwidth input, possibly provided in chip scale packaging, and may be combined with processing chip or circuit. The transmitter/receiver 43 may transmit and/or receive via for example an antenna 48. The transmitter/receiver 43 may also act as a controller and include circuitry and functionality for controlling the device 40, although a separate control unit may be used. Typically, the device may include a power source 45, such as one or more batteries. For example, the power source 45 may include silver oxide batteries, lithium batteries, or other electrochemical cells having a high energy density, or the like. Other power sources may be used.

Other components and sets of components may be used. For example, the power source may be capable of receiving power from an external power source transmitting power to the device 40, and a controller separate from the transmitter/receiver 43 may be used.

In one embodiment, the imager 47 may be a complementary metal oxide semiconductor (CMOS) imaging camera. The CMOS imager is typically an ultra low power imager and is provided in chip scale packaging (CSP). Other types of CMOS imagers may be used. In another embodiment, another imager may be used, such as a CCD imager, or another imager. According to other embodiments a 320×320 pixel imager may be used. Pixel size may be between 5 to 6 micron. According to some embodiments pixels may be each fitted with a micro lens.

Imager 47 may be fixed or otherwise attached to a substrate such as, for example, circuit board 64 or directly positioned onto a substrate 56. In other embodiments, circuit board 64 may be further attached to a substrate 56, which may for example support illumination source(s) 42 (which may be supported by its/their own substrate or circuit board, which may be supported by or integrated with substrate 56) and which may define a viewing direction 60 of device 40. Substrate 56 may be for example a rigid circuit board or a rigid-flex circuit board. In other embodiments, illumination source(s) may be positioned on a different plane than, for example, imager 47.

Preferably, located outside the patient's body in one or more locations, external to the in-vivo device 40, are a receiver 12, preferably including an antenna or antenna array 15, for receiving image and possibly other data from device 40, a receiver storage unit 16, for storing image and other data, a data processor 14, a data processor storage unit 19, and an image monitor 18, for displaying, inter alia, the images transmitted by the device 40 and recorded by the receiver 12. Typically, the receiver 12 and receiver storage unit 16 are small and portable, and are worn on the patient's body during recording of the images. Preferably, data processor 14, data processor storage unit 19 and monitor 18 are part of a personal computer or workstation, which may include components such as a processor or controller 21, a memory (e.g., storage 19, or other memory), a disk drive, and input-output devices, although alternate configurations are possible. In alternate embodiments, the data reception and storage components may be of another configuration. In addition, a data decompression module for decompressing data may also be included.

According to some embodiments of the present invention, a device such as device 40 may include a distance parameter measurement unit which may include an energy output unit or source, such as a dedicated collimated energy source 11. In some embodiments the energy source 11 may be provided for example, to measure and/or enable determination of the size of an in-vivo object and/or the distance of the in-vivo object from an in-vivo device, such as device 40. The energy source may reside externally to the device body, for example, in an extra-body unit. Other components or sets of components may be used.

The energy source 11 may be integrated within the in-vivo device 40, typically on at least one side of in-vivo device 40 but optionally in other locations. The energy source 11 may periodically or continually emit a light beam or illuminate, for example a point along a body lumen, which may be imaged, for example by the imager 47. The energy source 11 may include, for example, laser diodes, regular lenses and/or micro-lenses which may be attached to diodes/detectors, to enable generation and/or reception of point-wise illumination. In some embodiments one or more energy sources 11 may be provided, positioned on the side(s) and/or other locations of the circumference of the in-vivo device 40. In some embodiments a single energy source 11 may be provided.

An image data representing the illumination or light beam(s) transmitted by the energy source may be transferred, by transmitter/receiver 43, to a processor or controller unit, such as, for example, data processor 14. Alternatively, the processor or controller unit may be located within in-vivo device 40, such as, for example, within transmitter/receiver 43 or imager 47. This data may include for example image data of an object 215, the time at which the image was recorded, as well as any other related data, such as intensity, hue, and/or color. The time may be derived from, for example, an in-vivo device 40 master clock, which may be integrated into, for example, an ASIC as part of transmitter 43, reception unit 12, or any other component in in-vivo imaging system 100. In other embodiments, the time need not be transmitted. The data may be received by reception unit 12, or may be transferred directly to data processor 14. In addition to an image frame there may be a header which may include various telemetry data, such as temperature, pH, pressure, etc.

Figure 2A:
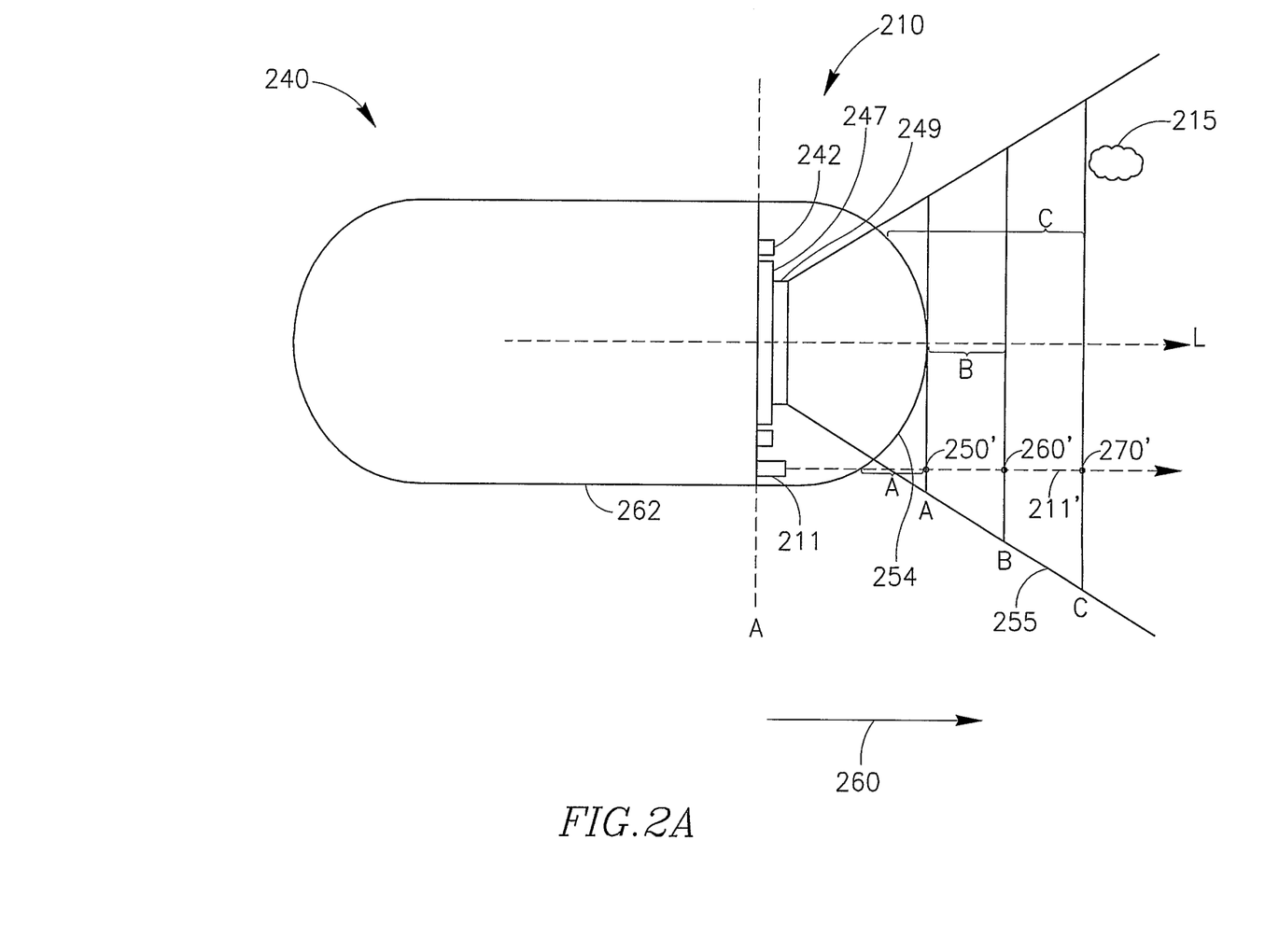
FIG. 2A shows a schematic diagram of an in-vivo imaging device, according to one embodiment of the present invention.

Reference is now made to FIG. 2A, a schematic two dimensional presentation of an in-vivo device 240 according to an embodiment of the present invention. Referring to FIG. 2A, optical system generally referenced as 210 may be included in, for example, device 40 of FIG. 1, but may be included in other suitable devices. Optical system 210 may include, for example, illumination source(s) 242, imager 247, and one or more lenses 249 disposed behind a viewing dome 254, for viewing, for example, a target or object 215. The optical system 210 may include an energy source 211 such as a collimated light source or laser source for measuring, for example the distance of the object 215 from the in-vivo device 240 (e.g. from the dome 254) and/or the size of the object 215. The one or more illumination source(s) 242 and the energy source 211 may be positioned, for example, such that perpendicular axis A intersects both the illumination source(s) 242 and the energy source 211.

According to some embodiments of the present invention, the dome 254 may be in one embodiment convex or substantially convex and smooth, and may project outward from the main body and/or housing 262 of device 240 in a "forward"

(and/or viewing) direction 260, although note that "forward" is a relative term, as in some embodiments in use the imaging section of device 240 may either lead or follow the rest of the device 240 as it traverses a body lumen. Dome 254 may typically provide for example a Field Of View 255 (FOV) for optical components, such as the imager 247 and the lenses 249 of the in-vivo device 240. For example, the device 240 may, depending on circumstance, traverse a body lumen such that the imager 247 the illumination source(s) 242 and the energy source 211 may face the substantially upstream and/or downstream direction, as device 240 may be designed so that there may be two possible directions of travel, both substantially parallel to the axis L of device 240. The direction of travel need not be parallel to the longitudinal axis L, and other configurations (e.g., spherical) may be used. In an embodiment where the device 240 has one or two possible directions of travel (e.g., downstream, or downstream and upstream), the forward end may be defined as being at the end of the device in which the device travels, or one of such ends. In one embodiment, the FOV 255 of the imager 247 via the optical system may be along the longitudinal axis L and towards the "front" end. The device 240 may typically collect images of objects, such as object 215, which may be located generally forward of the forward end of the device 240 (or backward if the device 240 may be facing upstream and progressing downstream), typically up to a 140 degree angle of view although other angles may be used.

Objects, generally beyond the "front" end, such as target or object 215, may be imaged, and the distance of the object 215 from device 240 (e.g. the dome 254) and/or the size of object 215 may be measured by illuminating or emitting for example a collimated light and/or laser beam 211' relative to a direction of travel or imaging of the device 240 e.g. in the direction of the longitudinal axis L.

Figure 2B:
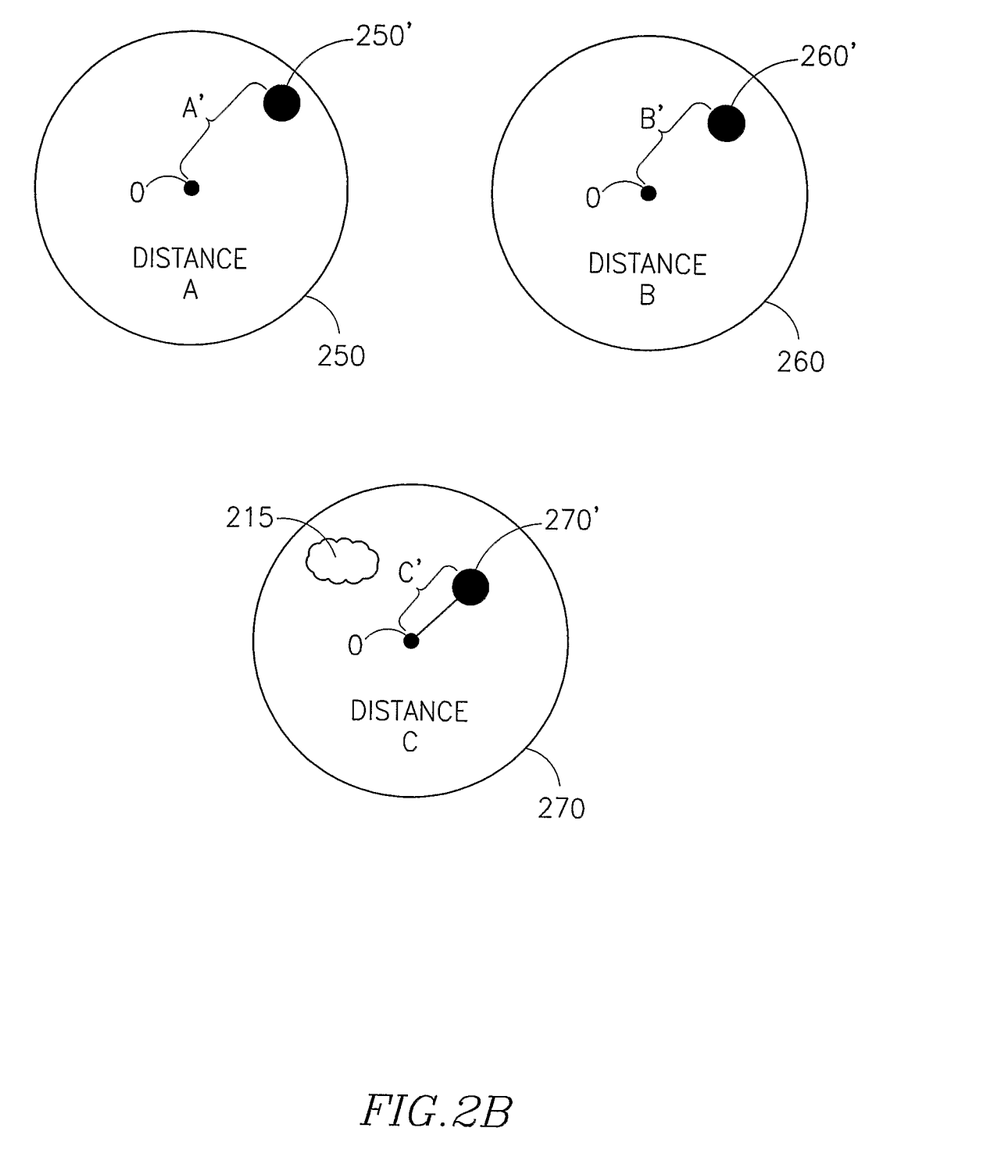
FIG. 2B shows a set of images captured by an in-vivo imaging device, according to an embodiment of the present invention.

Reference is now made to FIG. 2B showing a set of images 250, 260 and 270 which may be captured for example by the in-vivo device 240 of FIG. 2A, according to some embodiments of the present invention. As shown in FIGS. 2A and 2B points 250', 260' and 270' may represent the location of the laser beam 211' in each image 250, 260 and 270. In some embodiments points 250', 260' and 260' may be used for measuring the distance of in-vivo objects such as object 215 from the in-vivo device 240. The location of the laser beam image 211' (e.g. points 250', 260' and 270'), in images 250, 260 and 270 changes according to the distance of the captured image from the in-vivo device 240 e.g. the greater the distance between the laser beam 211' and the in-vivo device, the closer the image of the laser beam (e.g. points 250', 260' and 270') to the center of the image (point O). For example, in image 250 which represent an image captured at a distance A from the device 240 (e.g. 0 mm from the optical dome 254) point 250' is located at a distance A' from the center of image 250 (point O). In image 260 which represent an image captured at distance B from the device 240 (e.g. 10 mm from the optical dome 254) point 260' is located at a distance B' from point O (e.g. A'>B'), while in image 270 which represent an image captured at distance C from the device 240 (e.g. 20 mm from the optical dome 254) point 270' is located at a distance C' from point O (e.g. C'<B'<A').

The distance of in-vivo objects, such as the object 215, from the in vivo device 240 may be determined/measured by measuring the distance between the image of the laser beam 211' (points 250', 260' and 270') in the images 250, 260 and 270 and a random reference point in the images 250, 260 and 270, such as, for example, point O (the center of the image). For example, the distance between point 270' (e.g. laser beam 211') and point O in image 270 is C', which means that the distance of object 215 from the in vivo-device 240 (e.g. optical dome 254) is C (e.g. 20 mm). Thus, knowing, for example:

1. the distance of a target point or an in-vivo object in an image from an in-vivo device;
2. the number of pixels which the target point or the object captures in the image; and
3. the magnification of the optical system in the in-vivo device, it may be possible to measure and calculate, based on simple trigonometric calculations, the size of the in-vivo object or the target point, imaged by the in-vivo device, such as device 240. Such a size estimate may be, for example, provided to a user at a processing and/or display system. For many medical purposes, a range of sizes for an object such as provided by the above illustration may suffice. For example, the size of a polyp may correlate to its malignancy. Knowledge of the size of a polyp therefore may enable a physician or other user of a system in accordance with the present invention to decide about urgency of the treatment, type of the treatment, and tools required for the treatment.

Various suitable methods of determining the size and the distance or estimated distance of an in-vivo object, such as object 215, from an in-vivo device, e.g. device 240, may be used. According to another embodiment of the present invention, the intensity and/or size of the illumination or laser beam image (e.g. points 250', 260' and 270') correlates to the distance of for example laser beam, such as laser beam 211', emitting from the energy source 211, from the in-vivo device 240. For example point 270' imaged at a distance C (e.g. 20 mm) from the in-vivo device 240 (e.g. dome 254) will be less intensive than point 250' imaged at a distance A (e.g. 0 mm) from the from the in-vivo device (e.g. dome 254). This intensity of illumination may be measured by the data processor 14. Thus, for example, according to the intensity level of the image of the laser beam 211' (e.g. points 250', 260' and 270') the distance of in-vivo objects, (e.g. object 215) may be measured. Such distance or distance range may be used to calculate the estimated size of the object. In accordance with embodiments of the present invention, once the distance of an object, such as object 215, has been calculated, its size may be determined by simple trigonometric calculations.

Figure 3A:
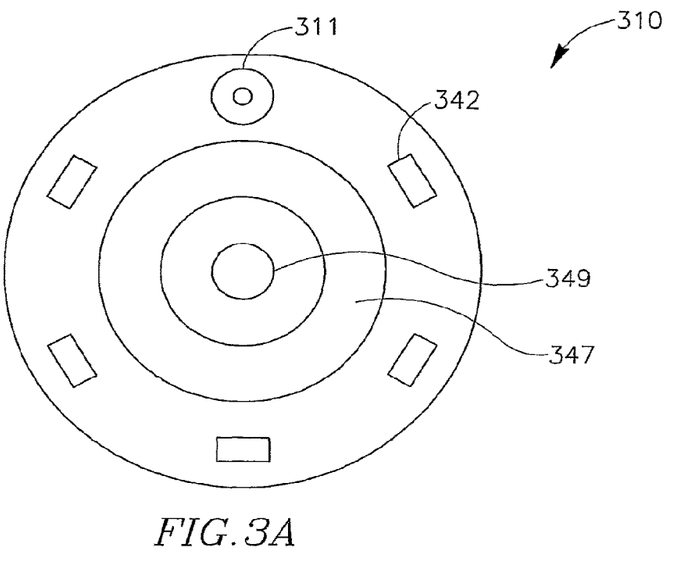
FIGS. 3A and 3B show a schematic two dimensional presentation of a top view and a side view of an optical system, according to an embodiment of the present invention.
Figure 3B:
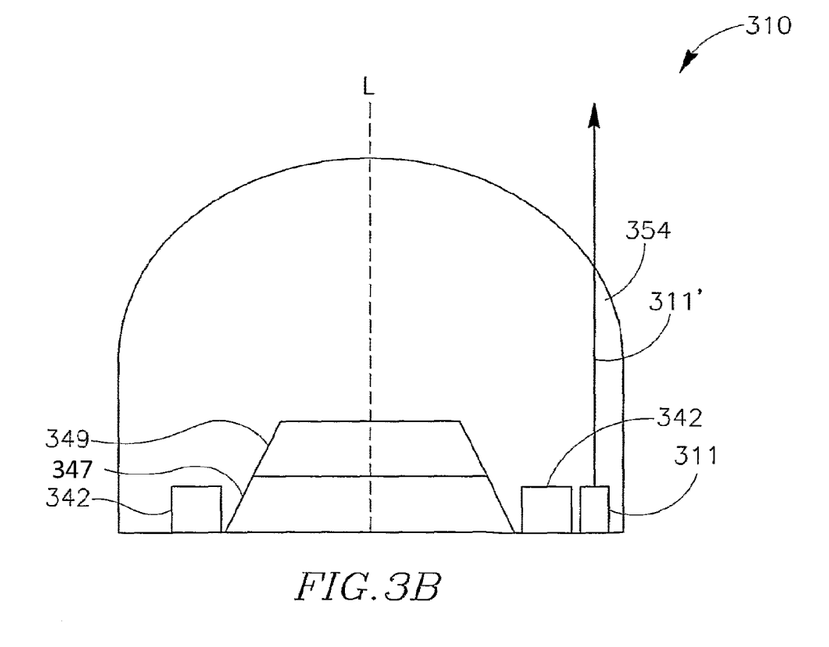

Reference is now made to FIGS. 3A and 3B, a schematic two dimensional presentation of a top view and a side view of an optical system according to an embodiment of the present invention. Referring to FIG. 3A, optical system generally referenced as 310 may be included in, for example, device 40 of FIG. 1, but may be included in other suitable devices, such as an endoscope, trocar, or other in-vivo imaging device. Optical system 310 may include, for example, illumination source(s) 342, imager 347, and one or more lenses 349 disposed behind a viewing window such as dome 354, for viewing, for example, a target or object. One, two, or more than two illumination sources may be used. An energy source 311, such as a laser diode for measuring the distance of an in-vivo object or target from an in-vivo device may be positioned, for example, in proximity to the illumination source(s) 342 the lenses 349 and/or imager 347.

According to some embodiments of the present invention, the energy source 311 may be positioned at a selected angle more than 0 and smaller than 180 degrees, relative to the longitudinal axis (L) of the optical system 310. Typically, the imager 347 and the lenses 349 face generally in the direction of axis L. Thus, the direction of the laser beam, which may be the direction in which the imager 347 is facing, may coincide with an axis (e.g., axis L) of the optical system 310. For example, the energy source 311 may be positioned in parallel to an axis L, e.g., a longitudinal axis L, of the optical system 310, such that laser beam 311' may be parallel to the direction of imaging. The direction of the laser beam 311' may be for example the direction in which most of the illumination of the illumination source(s) 342 is projected. Other arrangements are possible.

Figure 3C:
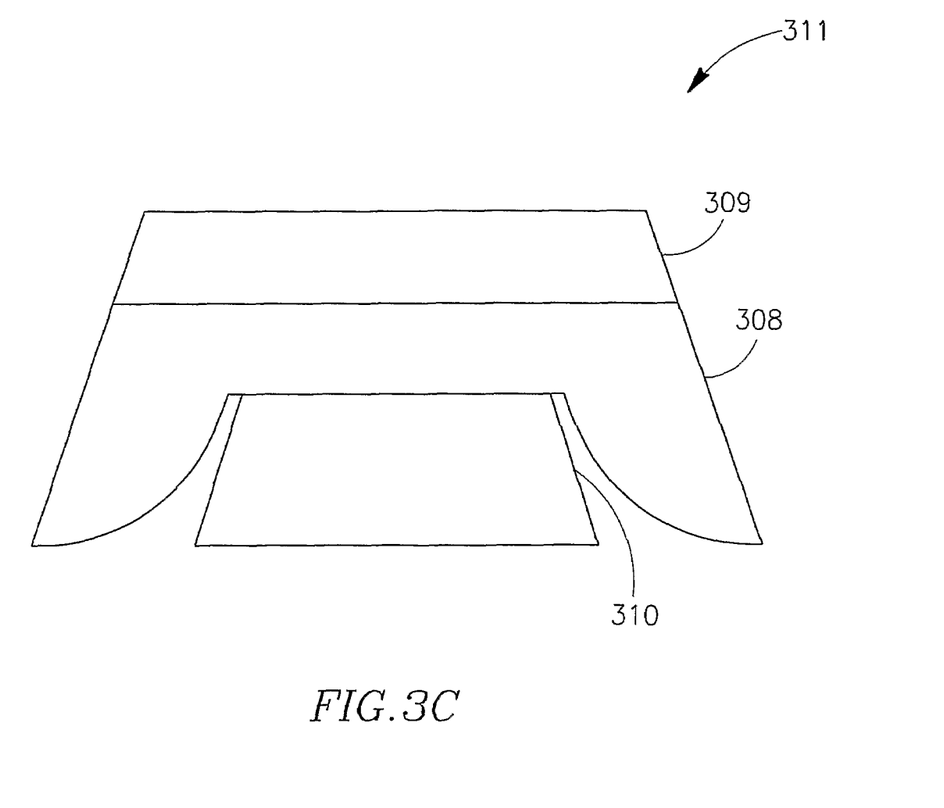
FIG. 3C shows a schematic diagram of an energy source, according to an embodiment of the present invention.

FIG. 3C illustrates an energy source 311 according to one embodiment of the present invention. The energy source 311, may include a laser diode 310 such as a Vertical Cavity Surface Emitting Laser (VCSEL) e.g. laser with a vertical cavity that emit light from their surface in contrast with regular "edge emitters". According to some embodiments the energy source may include a beam shaping unit e.g. a micro optical element such as a lens 309 and a lens holder 308 for holding, for example the lens 309.

Figure 4:
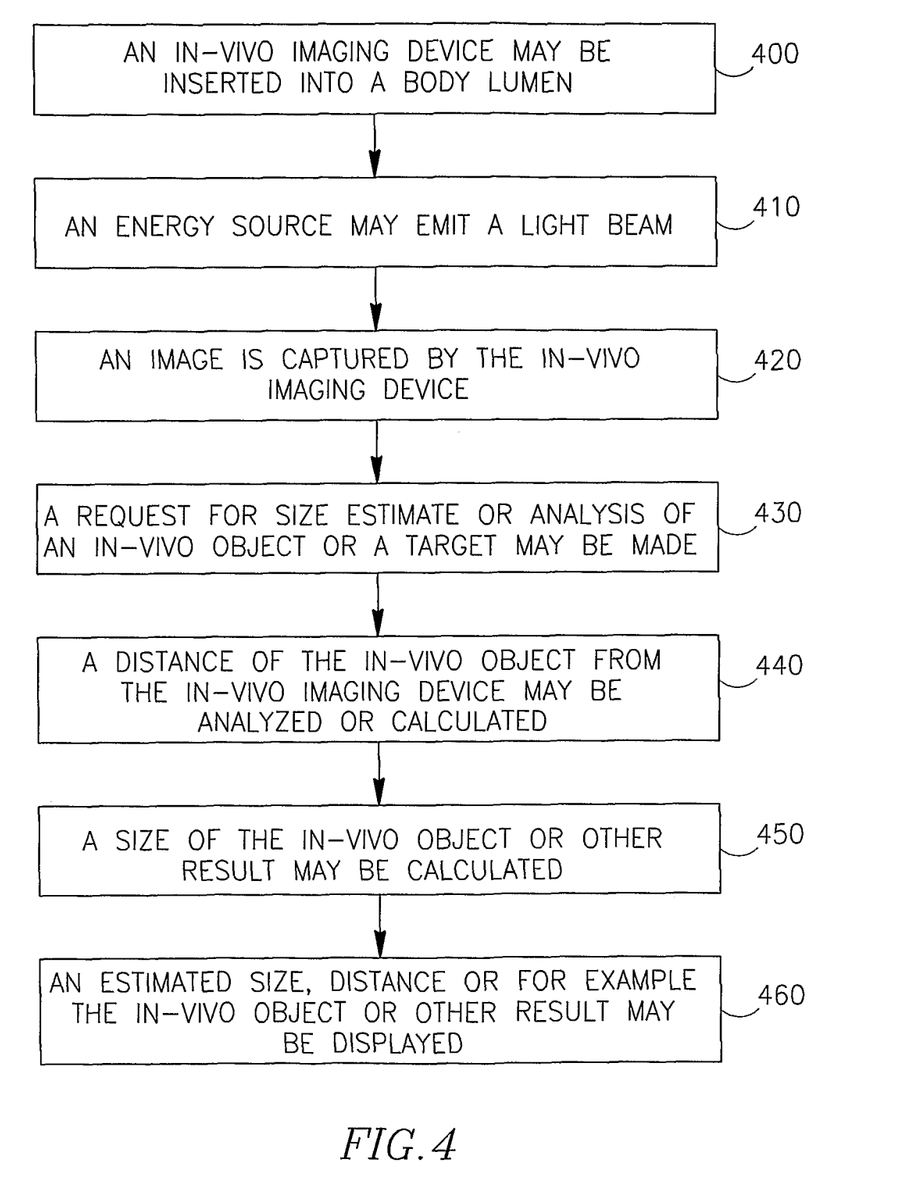
FIG. 4 is a flowchart of a method according to an embodiment of the present invention.

FIG. 4 depicts a series of steps of a method in accordance with an embodiment of the present invention. In step 400, an in-vivo device, for example an in-vivo imaging device may be inserted into a body lumen, for example by swallowing. In step 410 an energy source which may be part of an optical system of the in-vivo device may emit a light beam, such as a collimated light beam, or a laser beam. In step 420, an image is captured by the in-vivo imaging device. In step 430, a request for size estimate or analysis of an in-vivo object or a target may be made, for example, by a user's indicating on the image of the in-vivo object on a monitor or by the data processor using computer image analysis techniques. Such an explicit request need not be provided.

In step 440, a distance of the in-vivo object from the in-vivo imaging device may be analyzed or calculated. In step 450, a size of the in-vivo object or other result may be calculated for example based on the number of pixels the in-vivo object captures in the image, the distance of the in-vivo object from an in-vivo device, and the magnification of an optical system of the in-vivo device. In step 460, an estimated size, distance, of for example the in-vivo object, or other result may be displayed or otherwise provided. Other steps or series of steps may be used.

The user of an in-vivo imaging system employing an embodiment of the present invention may, for example estimate the size of an object viewed on the monitor or other image display device. This measurement estimate may be made manually or automatically. For example, by measuring the dimensions of an object viewed on the monitor, and as the magnification of the optical system of the in-vivo device and the distance of the object from the in-vivo device are known the user may estimate the size of the object according to simple trigonometric calculations.

Alternately, this estimation may be performed automatically. A user may, for example, choose two points on the display (e.g., using a mouse or other user interface with the processing unit), possibly corresponding to the edges of an object, and the data processor 14 unit may provide, for example the size of the object. Other methods of inputting a user indication of an object and outputting a size or size range may be used. Alternately, the data processor 14 or other unit may choose an object or distance on an object, for example an object identified using computer image analysis techniques. This may be particularly useful for example where polyps of a certain size range (e.g., 0.5 mm to 1.5 mm) may be diagnosed differently from a polyp of a larger size range (e.g., 1 cm-3 cm). Thus, in this example, using an embodiment of the present invention, even a range of sizes may provide useful for diagnosing one type of polyp or another.

While the invention has been described with respect to a limited number of embodiments, it will be appreciated that many variations, modifications and other applications of the invention may be made. Embodiments of the present invention may include apparatuses for performing the calculations and operations herein. Such apparatuses may be specially constructed for the desired purposes or may comprise general purpose computers selectively activated or reconfigured by a computer program stored in the computers. Such computer programs may be stored in a computer readable storage medium, such as, but is not limited to, any type of disk including floppy disks, optical disks, CD-ROMs, magnetic-optical disks, read-only memories (ROMs), random access memories (RAMs), electrically programmable read-only memories (EPROMs), electrically erasable and programmable read only memories (EEPROMs), magnetic or optical cards, or any other type of media suitable for storing electronic instructions.

The processes presented herein are not inherently related to any particular computer or other apparatus. Various general purpose systems may be used with programs in accordance with the teachings herein, or it may prove convenient to construct a more specialized apparatus to perform the desired method. The desired structure for a variety of these systems appears from the description herein. In addition, embodiments of the present invention are not described with reference to any particular programming language. It will be appreciated that a variety of programming languages may be used to implement the teachings of the invention as described herein.

Unless specifically stated otherwise, as apparent from the discussions herein, it is appreciated that throughout the specification discussions utilizing terms such as "estimating", "processing", "computing", "calculating", "determining", or the like, typically refer to the action and/or processes of a computer or computing system, or similar electronic computing device (e.g., a "computer on a chip" or ASIC), that manipulate and/or transform data represented as physical, such as electronic, quantities within the computing system's registers and/or memories into other data similarly represented as physical quantities within the computing system's memories, registers or other such information storage, transmission or display devices.

It will be appreciated by persons skilled in the art that the present invention is not limited to what has been particularly shown and described hereinabove. Rather the scope of the present invention is defined only by the claims, which follow:

What is claimed is:

1. An in-vivo device comprising:
an illumination source to illuminate a body lumen;
an energy source to emit a light beam in the body lumen to create a point of light in the body lumen;
an imager to image the point of light and an illuminated object in the body lumen; and
a processor configured to:
receive an image of the body lumen, the image including the point of light, the illuminated object and a reference center point of the image,
determine a distance between the illuminated object and the in-vivo imaging device based on the distance of the point of light from the reference center point; and
determine a size of the illuminated object based on said distance determination.

2. The device according to claim 1, wherein the energy source is a laser diode.

3. The device according to claim 2, wherein the laser diode is a Vertical Cavity Surface Emitting Laser.

4. The device according to claim 1, comprising a transmitter.

5. The device according to claim 1, comprising an antenna.

6. The device according to claim 1, wherein the in-vivo device is an autonomous swallowable capsule.

7. The device according to claim 1, wherein the object is a polyp.

8. An in-vivo imaging system comprising:
   an in-vivo imaging device, the device comprising an imager, an illumination source and an energy source to emit a light beam in a body lumen; and
   a processor configured to;
      receive from the in-vivo device an image of a point of light created by the light beam, objects illuminated by the illumination source, and a reference center point of the image;
      determine a distance between the illuminated objects and the in-vivo imaging device based on the distance of the point of light from the reference center point; and
      determine a size of the illuminated object based on said distance determination.

9. The system according to claim 8, wherein the processor calculates an estimated size of objects in the image.

10. The system according to claim 8, wherein the processor calculates an intensity of the point of light in the image.

11. The system according to claim 8, wherein the processor calculates a number of pixels which capture the object in the image.

12. A method for estimating a size of an in-vivo object, using images acquired by an in-vivo imaging device, the method comprising:
   emitting a light beam from an imaging device from within a body lumen, wherein the imaging device comprises an energy source for emitting the light beam and an illumination source for illuminating the body lumen;
   obtaining an image of the body lumen, a point of light created by the light beam on a body lumen wall and a reference center point of the image; and
   determining the distance between an in-vivo object and the in-vivo imaging device based on the distance of the point of light from the reference center point; and
   determining the size of the illuminated object based on said distance determination.

13. The method according to claim 12, comprising measuring an intensity of the point of light in the image.

14. The method according to claim 12, comprising calculating a number of pixels the object captures in the image.

15. The method according to claim 12, comprising estimating a size of the object according to a number of pixels that capture the object in the image, a distance of the object from the in-vivo device, and a magnification of an optical system of the in-vivo device.

16. The device according to claim 2, wherein the energy source further comprises an optical means to enable generation and/or reception of point-wise illumination.

17. The device according to claim 1, wherein the point of light is identifiable in the image taken by the imager.

* * * * *